US00PP22565P2

(12) United States Plant Patent
Dobres

(10) Patent No.: US PP22,565 P2
(45) Date of Patent: Mar. 6, 2012

(54) ***COREOPSIS* PLANT NAMED 'NOVCORCAR'**

(50) Latin Name: *Coreopsis verticillata*
Varietal Denomination: Novcorcar

(75) Inventor: Michael S. Dobres, Philadelphia, PA (US)

(73) Assignee: NovaFlora Inc., West Grove, PA (US)

( * ) Notice: Subject to any disclaimer, the term of this patent is extended or adjusted under 35 U.S.C. 154(b) by 0 days.

(21) Appl. No.: 12/805,688

(22) Filed: Aug. 13, 2010

(51) Int. Cl.
*A01H 5/00* (2006.01)

(52) U.S. Cl. ..... Plt./417

(58) Field of Classification Search ..... Plt./417
See application file for complete search history.

*Primary Examiner* — June Hwu
(74) *Attorney, Agent, or Firm* — Buchanan Ingersoll & Rooney PC

(57) ABSTRACT

The present *Coreopsis verticillata* cultivar was created by the gamma-ray mutagenesis of the 'Crème Brulée' cultivar. An upright outwardly spreading mounding growth habit is displayed as well as a freely basal branching habit. Lacy bright green foliage is formed. Attractive, smaller daisy-type inflorescences are formed. The plant further can be distinguished by an observation of its less elongated terracotta-colored ray florets. The plant displays a propensity to freely flower for an extended period of time. The plant can be grown to advantage as attractive ornamentation in parks, gardens, and residential settings.

2 Drawing Sheets

Figure 1:
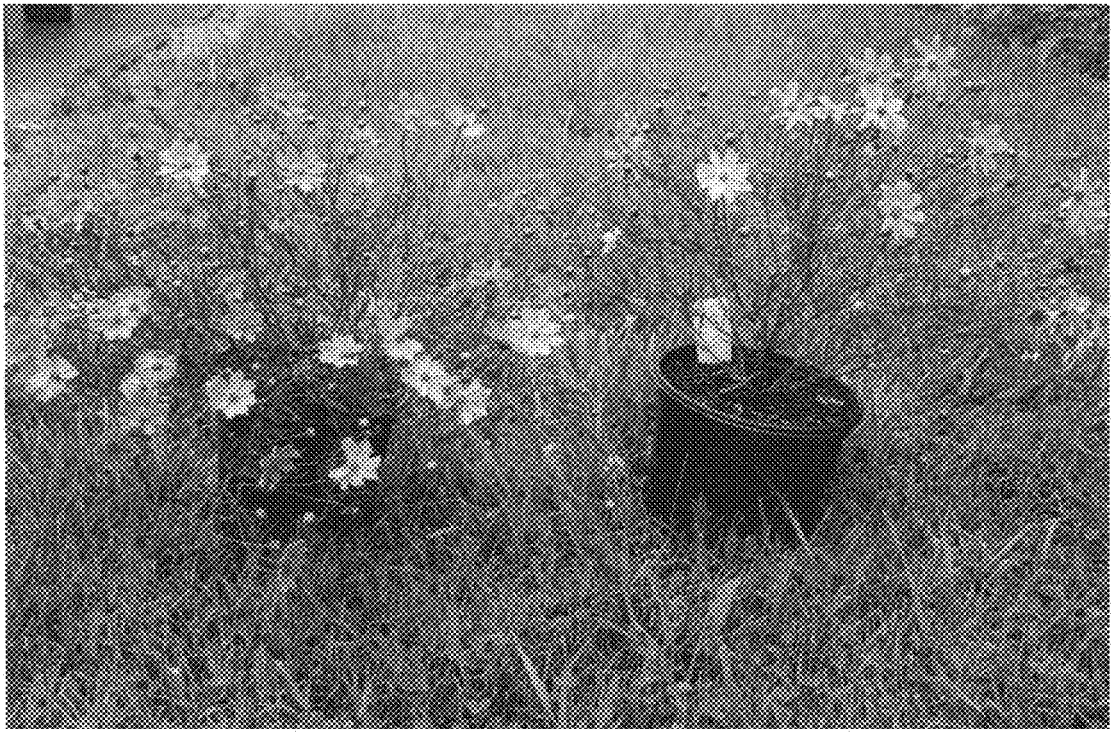

Botanical/commercial classification: *Coreopsis verticillata*/Thread-leaf *Coreopsis*.

Varietal denomination: cv. Novcorcar.

SUMMARY OF THE INVENTION

Plants of *Coreopsis verticillata* sometimes bear common names such as thread-leaf coreopsis, whorled coreopsis, thread-leaved tickseed, and pot-of-gold.

The 'Crème Brulée' cultivar (U.S. Plant Pat. No. 16,096) originated as a naturally-occurring whole plant mutation of the 'Moonbeam' cultivar (non-patented in the United States). The inflorescence of the 'Crème Brulée' is darker yellow than that of the 'Moonbeam' cultivar (non-patented in the United States).

The 'Sienna Sunset' cultivar (U.S. Plant Pat. No. 20,470) originated as a naturally occurring branch mutation of the 'Crème Brulée' cultivar, and displays apricot-colored ray florets.

An additional new and distinct cultivar of *Coreopsis verticillata* now is provided. The new cultivar of the present invention originated through the induced mutagenesis of in vitro cultures of the 'Crème Brulée' cultivar, followed by selection. More specifically, the 'Crème Brulée' cultivar while present in tissue culture underwent treatment during April 2006 with gamma radiation. The resulting cultures following exposure to such radiation were rooted during July 2006 near West Grove, Pa., U.S.A. The rooted plants thereafter were grown in huts with minimal heat during the following winter. During the spring and summer of 2007, the phenotypes of the plants underwent detailed study. A single plant of the present invention was selected and has thereafter been carefully preserved primarily in view of the distinctive character of its flowers. Had this plant not been selected and preserved, it would have been lost to mankind.

It was found that the new *Coreopsis verticillata* plant displays the following combination of characteristics:

(a) displays an upright outwardly spreading and mounded growth habit,
(b) displays a freely basal branching habit,
(c) displays lacy bright green foliage,
(d) displays a propensity to freely flower for an extended period of time, and
(e) forms attractive daisy-type inflorescences which when compared to the 'Sienna Sunset' cultivar are smaller in size and display less elongated darker terracotta-colored ray florets.

Additionally, it has been found that the stems of the new cultivar tend to be more upright than those of 'Sienna Sunset' cultivar, and the new cultivar tends to assume a more dense growth habit than that of the 'Sienna Sunset' cultivar.

The new cultivar readily can be distinguished from the 'Moonbeam', 'Crème Brulée' and 'Sienna Sunset' cultivars upon an inspection of the blossom colorations as previously indicated.

The new cultivar does not require pinching; however, the plants tend to be sturdier and even more dense when pinched.

The new cultivar can be grown to provide attractive ornamentation in parks, gardens, and residential settings.

Asexual reproduction of the new cultivar in a controlled environment by the rooting of cuttings has been conducted near West Grove, Pa., U.S.A., beginning in 2007. It has been demonstrated that the combination of characteristics of the new cultivar, including its distinctive blossom coloration, is firmly fixed and is well retained in succeeding generations. Accordingly, the new cultivar can be asexually reproduced in a true-to-type manner.

The new cultivar has been named 'Novcorcar'.

The 'Novcorcar' plant has not been observed under all possible environmental conditions to date. Accordingly, it is possible that the phenotype may vary somewhat with variations in the environment, such as temperature, light, day length, contact with pesticides, etc.

BRIEF DESCRIPTION OF THE PHOTOGRAPHS

The accompanying photographs were prepared during July 2009 and illustrate a typical plant and flower of the new cultivar, as well as a plant and flower of the 'Sienna Sunset' cultivar for comparative purposes. Such plants were grown outdoors near West Grove, Pa., U.S.A., in one-gallon containers and were approximately 3 to 4 months in age.

FIG. 1 illustrates on the left a plant of the new 'Novcorcar' cultivar and on the right a plant of the 'Sienna Sunset' cultivar. The 'Novcorcar' cultivar is shown to display inflorescence wherein the ray florets are of a darker terracotta coloration. Also, the 'Novcorcar' plant displays a denser and somewhat more upright overall growth habit.

Figure 2:
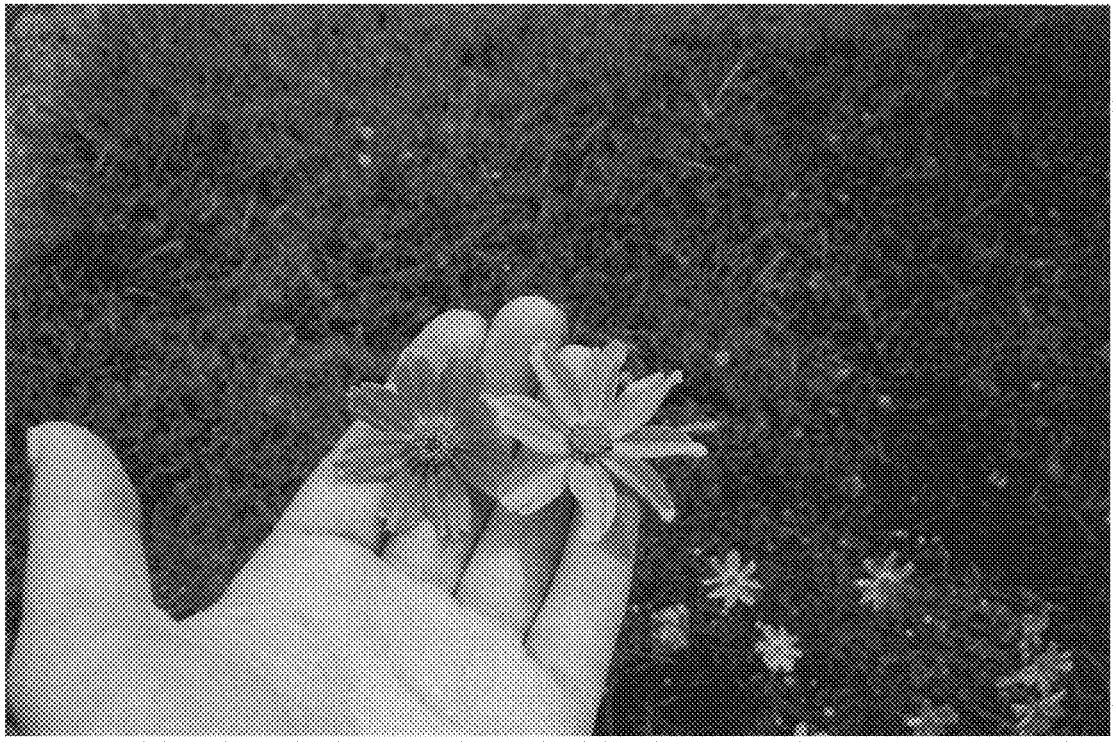

FIG. 2 illustrates on the left a typical blossom of the 'Novcorcar' cultivar and on the right a typical blossom of the 'Sienna Sunset' cultivar. The 'Novcorcar' cultivar blossom is shown to exhibit a lesser diameter than that of the 'Sienna Sunset' cultivar and disc florets are less elongated and of a darker terracotta coloration.

DETAILED DESCRIPTION

The chart used in the identification of the colors described herein is The R.H.S. Colour Chart (1995) of The Royal Horticultural Society, London, England. In some instances, more common color terms are provided and are to be accorded their usual dictionary significance. The plants had been asexually reproduced by the rooting of cuttings, were approximately three to four months of age, had been pinched, and were observed while growing outdoors in full sun in one-gallon containers during June near West Grove, Pa., U.S.A.

Botanical classification: *Coreopsis verticillata.*

Cultivar: 'Novcorcar'

Plant:

*Habit.*—Herbaceous perennial, upright outwardly spreading and mounded with flowers generally positioned at the level of the plant canopy.

*Height.*—Approximately 34 cm on average.

*Width.*—Approximately 54 cm on average.

*Lateral branches.*—Freely basal branching with two laterals commonly developing at each node.

*Branch length.*—Commonly approximately 33 cm on average.

*Branch diameter.*—Commonly approximately 3 mm on average.

*Internode length.*—Commonly approximately 3.4 cm on average.

*Branch texture.*—Pubescent.

Foliage:

*Arrangement.*—Opposite, single, sessile.

*Length.*—Variable, commonly approximately 1.5 to 4 cm.

*Width.*—Commonly approximately 3 mm on average at the widest point.

*Shape.*—Spatulate and occasionally trifid.

*Apex.*—Acute.

*Base.*—Attenuate.

*Margin.*—Entire.

*Texture.*—Pubescent on the upper and under surfaces.

*Color.*—When developing and fully expanded, the upper surface is near Green Group 137B and the under surface is near Green Group 137C.

Flowering description:

*Appearance.*—Large daisy-type composite inflorescence form with elongated oblong-shaped ray florets. Inflorescences are borne on terminals arising from leaf axils. Disc and ray florets develop acropetally on a capitulum.

*Flowering response.*—Under normal conditions, plants flower from late June to September in southeastern Pa., U.S.A.

*Inflorescence longevity.*—Individual inflorescences commonly last approximately one to two weeks, depending upon environmental conditions.

*Quantity of inflorescences.*—Very freely flowering, commonly with approximately 70 to 90 buds and inflorescences per plant.

*Buds.*—Commonly spherical in shape, approximately 6 to 7 mm in length on average, approximately 6 to 7 mm in diameter on average, and commonly a blend of Greyed-Orange Group 172B and Greyed-Red Group 178B in coloration.

*Inflorescence diameter.*—Commonly approximately 2.3 to 3.4 cm when fully open. This is smaller than the flower diameter commonly displayed by the 'Crème Brulée' and 'Sienna Sunset' cultivars.

*Inflorescence depth.*—Commonly approximately 1.2 cm on average.

*Disc.*—Commonly approximately 4 mm on average. This is smaller than the disc diameter commonly displayed by the 'Crème Brulée' and 'Sienna Sunset' cultivars.

*Fragrance.*—None detected.

*Ray florets.*—Aspect: initially upright and concave, and when mature substantially perpendicular to peduncle and mostly flat. shape: elongated oblong, and generally with less elongation than the 'Crème Brulée' and 'Sienna Sunset' cultivars. length: approximately 1.6 cm on average. width: approximately 1.3 cm on average. apex: emarginate, deeply infused, and jagged. base: attenuate with short corolla tube. corolla tube length: commonly approximately 3.5 mm. margin: entire. texture: smooth, glabrous, and velvety on the upper and lower surfaces. number: approximately eight arranged in a single whorl. color: when opening near Greyed-Orange Group 173A, and when fully open the upper surface commonly is near Greyed-Orange Group 173B and the under surface is near Greyed-Orange Group 164B. Such coloration is substantially darker than that of the 'Crème Brulée' and 'Sienna Sunset' cultivars as previously indicated.

*Disc florets.*—Arrangement: massed at the center of the inflorescence. shape: tubular, flared at the apex, and with five-pointed apices. number: approximately 88 on average. length: commonly approximately 2.5 mm. width: commonly approximately 1 mm at the base. color: near Yellow-Orange Group 15A towards the apex, and near Yellow-Green Group 15A towards the base.

*Reproductive organs.*—Location: androecium and gynoecium present only among disc florets. stamen number: five per floret. anther length: approximately 1 mm. anther color: near Greyed-Purple Group 187A commonly with more brown. pollen quantity: moderate. pollen color: near Yellow-Orange Group 17A. pistil number: one per floret. pistil length: approximately 1 mm. stigma shape: bi-parted. stigma color: near Yellow Group 9A to Yellow Group 12A. style color: near Yellow Group 9A. receptacle: substantially round in configuration, commonly approximately 0.5 cm in diameter, and near Yellow-Green Group 144A in coloration.

*Involucral bracts.*—Length: approximately 0.7 cm on average. number: 8. shape: broadly lanceolate with a truncated base. disposition: organized in a single row around the receptacle. texture: smooth and waxy on upper and lower surfaces. color: commonly near Yellow-Green Group 144A overlaid with Yellow Group 12A.

*Pecuncle.*—Length: approximately 10 cm on average. strength: relatively strong. texture: the surface is smooth. colon near: Yellow-Green Group 144A. seeds/fruit: none encountered during observation to date.

Disease resistance: Resistance to common diseases, such as Powdery Mildew, is believed to be comparable to other *Coreopsis* plants.

Hardiness: Hardy in U.S.D.A. Hardiness Zone Nos. 7 to 9. Some winter protection may be needed to reliably grow as a perennial in U.S.D.A. Hardiness Zone No. 6.

I claim:

1. A new and distinct cultivar of *Coreopsis verticillata* plant, substantially as herein described, which:

(a) displays an upright outwardly spreading and mounded growth habit, (b) displays a freely basal branching habit, (c) displays lacy bright green foliage, (d) displays a propensity to freely flower for an extended period of time, and (e) forms attractive daisy-type inflorescences which when compared to the 'Sienna Sunset' cultivar (U.S. Plant Pat. No. 20,470) are smaller in size and display less elongated darker terracotta-colored ray florets; substantially as illustrated and described.

* * * * *